US010261094B2

(12) United States Patent
Rajadhyaksha et al.

(10) Patent No.: US 10,261,094 B2
(45) Date of Patent: Apr. 16, 2019

(54) COMPETITIVE LIGAND BINDING ASSAY FOR DETECTING NEUTRALIZING ANTIBODIES

(71) Applicant: Regeneron Pharmaceuticals, Inc., Tarrytown, NY (US)

(72) Inventors: Manoj Rajadhyaksha, Colchester, CT (US); Michael Partridge, Eastchester, NY (US); Albert Torri, Lagrangeville, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 0 days.

(21) Appl. No.: 15/031,126

(22) PCT Filed: Oct. 30, 2014

(86) PCT No.: PCT/US2014/063034
§ 371 (c)(1),
(2) Date: Apr. 21, 2016

(87) PCT Pub. No.: WO2015/066259
PCT Pub. Date: May 7, 2015

(65) Prior Publication Data
US 2016/0252520 A1 Sep. 1, 2016

Related U.S. Application Data

(60) Provisional application No. 61/898,046, filed on Oct. 31, 2013.

(51) Int. Cl.
G01N 33/53 (2006.01)
G01N 33/68 (2006.01)

(52) U.S. Cl.
CPC ..... G01N 33/6854 (2013.01); G01N 33/5306 (2013.01); G01N 2333/705 (2013.01)

(58) Field of Classification Search
None
See application file for complete search history.

(56) References Cited

U.S. PATENT DOCUMENTS

| 4,208,479 | A | * | 6/1980 | Zuk | C07J 41/0016 435/7.72 |
|---|---|---|---|---|---|
| 2010/0016228 | A1 | | 1/2010 | Gautier et al. | |
| 2010/0209926 | A1 | | 8/2010 | Alaoui et al. | |
| 2012/0034212 | A1 | * | 2/2012 | Bowen | C07K 16/248 424/133.1 |
| 2013/0108631 | A1 | | 5/2013 | Parussini et al. | |
| 2013/0266963 | A1 | | 10/2013 | Hauenstein et al. | |
| 2014/0193427 | A1 | * | 7/2014 | Lerner | C07K 16/22 424/158.1 |

FOREIGN PATENT DOCUMENTS

| JP | 2013-527444 A | 6/2013 |
|---|---|---|
| RU | 2 370 775 C2 | 10/2009 |
| WO | WO 2009/017226 A1 | 2/2009 |
| WO | WO 2009/020142 A1 | 2/2009 |
| WO | WO 2011/022725 A2 | 2/2011 |
| WO | WO 2011/113013 A2 | 9/2011 |
| WO | WO 2013/053751 A1 | 4/2013 |
| WO | WO 2013/071055 A1 | 5/2013 |

OTHER PUBLICATIONS

Belomestnov et al. (Arthritis & Rheumatism 2012 vol. 64, supplement S576).*
Spengler M et al: "Immuno-PCR assays for immunogenicity testing", Biochemical and Biophysical Research Communications, Academic Press Inc., Orlando, FL, US, vol. 387, No. 2, (Sep. 18, 2009) pp. 278-282.
Loyet, K M et al: "Technology comparisons for anti-therapeutic antibody and neutralizing antibody assyas in the context of an anti-TNF pharmacokinetic study", Journal of Immunological Methods, Elsevier Science Publishers B.V., Amsterdam, NL, vol. 345, No. 1-2 (Jun. 30, 2009) pp. 17-28.
Alvydas, Mikulskis et al: "Solution ELISA as a platform of choice for development of robust, drug tolerant immunogenicity assays in support of drug development", Journal of Immunological Methods, Elsevier Science Publishers B.V., Amsterdam, NL, vol. 365 No. 1 (Nov. 10, 2010) pp. 38-49.
Stubenrauch K et al: Subset analysis of patients experiencing clinical events of a potentially immunogenic nature in the pivotal clinical trials of tocilizumab for rheumatoid arthritis: Evaluation of an antidrug antibody ELISA using clinical adverse event-driven immunogenicity testing, Clinical Therapeutics, Excerpta Medica, Princeton, NJ, US, vol. 32, No. 9 (Aug. 1, 2010) pp. 1597-1609.
Terpe et al.,: "Overview of tag protein fusions: from molecular and biochemical fundamentals to commercial systems", Appl. Microbiol. Biotechnol 2003 vol. 60 pp. 523-533.
International Search Report and Written Opinion for PCT/US14/063034 dated Feb. 2, 2015.
Wu et al., "Competitive Ligand-Binding Assays for the Detection of Neutralizing Antibodies," Detection and Quantification of Antibodies to Biopharmaceuticals: Practical and Applied Considerations, Jun. 20, 2011, Chapter 10, pp. 175-192.

(Continued)

Primary Examiner — Changhwa J Cheu
(74) Attorney, Agent, or Firm — Cooley LLP; Ivor R. Elrifi; Matthew Pavao

(57) ABSTRACT

A immunogenicity assay for detecting the presence of neutralizing antibodies to a biotherapeutic protein wherein the biotherapeutic protein has been administered to a patient in need, comprising the steps of (a) obtaining a sample from the patient; (b) incubating the sample in the presence of a capture reagent; and (c) adding a detecting reagent, wherein a decreased signal relative to a control sample indicates the presence of a neutralizing antibody to the biotherapeutic agent.

29 Claims, 12 Drawing Sheets

(56) References Cited

OTHER PUBLICATIONS

Martins, T. B. et al., "Cell-Based Reporter Gene Assay for Therapy-Induced Neutralizing Antibodies to Interferon-Beta in Multiple Sclerosis," Journal of Interferon & Cytokine Research, vol. 33, No. 2, 2013, pp. 52-57.

Ngo, T. and Lenhoff, I. G. "Visual enzyme immunometric assay," 1988, Mir, 446 sh., Chapter 24, pp. 394-397 and English translation (6 pp. provided).

\* cited by examiner

COMPETITIVE LIGAND BINDING ASSAY FOR DETECTING NEUTRALIZING ANTIBODIES

CLAIM OF PRIORITY

This is the United States National Stage of Patent Cooperation Treaty Application No. PCT/US14/63034 filed Oct. 30, 2014, which claims priority to U.S. Provisional Patent Application No. 61/898,046 filed Oct. 31, 2013, the disclosures of which are incorporated herein by reference in their entireties.

FIELD

The present invention relates to assay methods for detecting the presence of neutralizing antibodies (Nab) against a biologic biotherapeutic.

BACKGROUND

The detection of antibodies, such as neutralizing antibodies (NAbs), is part of the immunogenicity assessment that this performed for patients treated with a biotherapeutic agent. Neutralizing antibodies neutralize the function of the drug thereby negatively impacting the efficacy of the drug. The presence of NAbs in patients treated with a specific biotherapeutic agent may be detected using several immunoassay methods, including, for example, colorimetric enzyme-linked immunosorbent assay (ELISA), immunofluorescence based receptor binding assays, soluble and solid phase radioimmunoassays, and sensor-based assay.

NAbs can also be detected using cell-based assays. In these cell-based assays, the presence of NAbs can be detected by their ability to inhibit the biological action of the biotherapeutic agent, for example, modulation of a biological process in the target cell. These assays may involve, for example, the activation of a reporter gene, such as luciferase or beta-galactosidase. However, these current detection methods suffer from a number of drawbacks including the level of sensitivity, the level of specificity, matrix interference issues, assay variability, limited dynamic range and the lengthy duration of the assays.

Sarilumab is the first fully human monoclonal antibody targeting the interleukin-6 (IL6) receptor in clinical development. IL-6 is a pleiotropic cytokine produced by immune and non-immune cells that plays a crucial role in regulation of immune response, acute-phase reactions, and hematopoiesis. It binds to soluble and cell membrane bound IL-6R ($\alpha$ chain) forming a binary complex and this complex is able to interact with cell membrane bound gp130 ($\beta$ chain), induces formation of signaling complex comprising two each of IL-6, IL-6R, and gp130.

SUMMARY

There is regulatory need to develop sensitive and reproducible assays that detect Nab activity in clinical samples. While cell-based assays are known in the art for detecting NAbs, non-cell based competitive ligand binding (CLB) assays can serve as a better alternative as they provide superior dynamic range and sensitivity. However, CLB assays can also have issues with interference from various assay and matrix components. Applicants have developed a sensitive and reliable CLB assay that can detect a neutralizing antibody (NAbs) response to a biotherapeutic drug molecule, in a patient.

In one aspect, a method for the assessment of a neutralizing antibody (NAb) to a biotherapeutic in a patient treated with a biotherapeutic is provided. The method encompasses assessment of the presence of NAbs during and/or post treatment of a patient treated with a biobiotherapeutic agent.

In one embodiment, the method for detecting the presence of neutralizing antibodies to a biotherapeutic protein, in a patient in need of the biotherapeutic protein and treated with said protein, the method comprises the steps of (a) combining a patient sample with a capture reagent, and (b) adding a detection reagent, wherein a decreased signal relative to a control sample indicates the presence of a neutralizing antibody to the biotherapeutic agent. In one embodiment, the protein biotherapeutic is a monoclonal antibody (mAb), preferably an anti-interleukin-6 receptor $\alpha$ (IL-6R$\alpha$) monoclonal antibody. In one embodiment, the protein biotherapeutic mAb is sarilumab or tocilizumab; more specifically the protein biotherapeutic mAb is sarilumab.

The sample is obtained from a patient being treated for an IL-6-dependent disease. Samples obtained from a patient include for example tissue, saliva, milk, blood, plasma, serum or any other related biological fluids in which antibodies can be detected. In one embodiment, the sample is a serum sample obtained from such a patient.

Examples of IL-6-dependent diseases include rheumatoid arthritis, diabetes, atherosclerosis, Alzheimer's disease, systemic lupus erythematosus, multiple myeloma, all mixed connective tissue disorders, Castleman's disease and prostate cancer. In a specific embodiment, a serum sample is obtained from a patient suffering from rheumatoid arthritis.

In an embodiment of the method, the capture reagent comprises the labeled biotherapeutic protein. When a patient is being treated with sarilumab, the capture reagent is labeled sarilumab. In some embodiments, the capture reagent is tagged with a label to facilitate binding to a matrix, surface, or counter-labeled molecule. Labels include for example biotin, avidin, streptavidin, polyarginine, polyhistidine, FLAG, c-myc, HAT (natural histifdine affinity tag), glutathione S-transferase, glutathione, S, S-fragment of RNaseA, maltose-binding protein, chitin-binding domain, chitin, calmodulin, calmodulin-binding peptide, and the like. See Terpe, K., "Overview of tag protein fusions: from molecular and biochemical fundamentals to commercial systems," Appl. Microbiol. Biotechnol. (2003) 60:523-533. In one embodiment of the method of the invention, the capture reagent is biotinylated sarilumab.

In an embodiment of the method, the detection reagent is labeled soluble IL-6 receptor $\alpha$. In another embodiment, the detection reagent contains a label to enable detection. Labels include for example chelated lanthanide series metals like europium, platinum group metals like ruthenium, fluorochromes, including inter alia xanthene derivatives like fluorescein and rhodamine, fluorescent proteins like green fluorescent protein (GFP) and its derivatives yellow fluorescent protein (YFP) and red fluorescent protein (RFP), radiolabels like iodine-125 and actinium-225, and other like detectable labels. In a more specific embodiment, the detection reagent is ruthenium labeled soluble IL-6 receptor $\alpha$.

In one embodiment, the combined patient sample and capture reagent are subjected to treatment with low pH (acidic). In a specific embodiment, the treatment is with acetic acid, which is then followed by a neutralization step.

In one embodiment, the assay method of the invention for detecting the presence of neutralizing antibodies in a patient being treated with a biotherapeutic protein exhibits a sensitivity of about 150 ng/mL, a drug tolerance of about 500 ng/mL, and a target interference tolerance of about 1 µg/mL.

In another aspect, a kit comprising the capture and detection reagents described above, and instructions for their use is provided.

FIGURES

Figure 7:
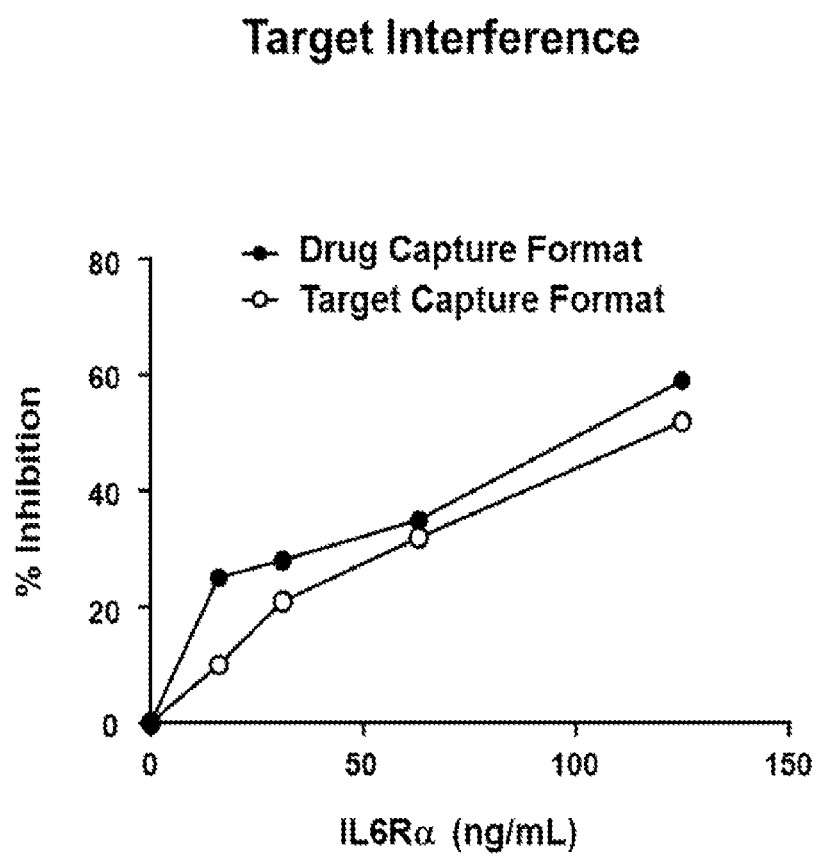
Figure 8:
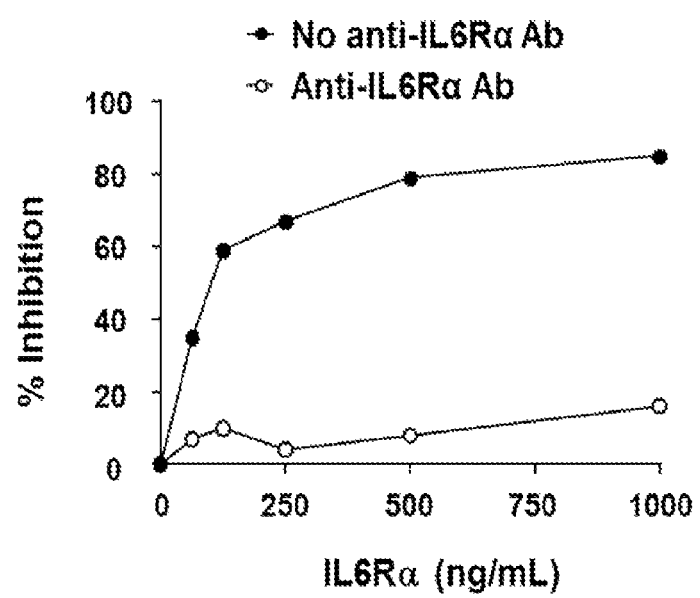

FIGS. 7 and 8 are graphs of the effect of IL6Rα interference on the generation of false positives. FIG. 7 shows the results for both drug capture and target capture formats; FIG. 8 shows the results of target interference in the presence of anti-target antibody using the drug capture format.

Figure 9:
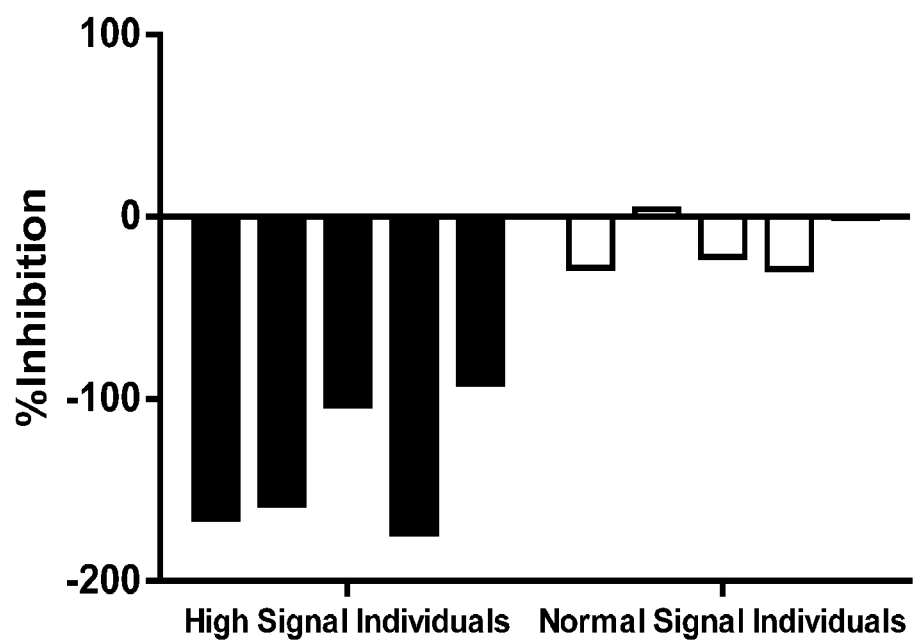
Figure 10:
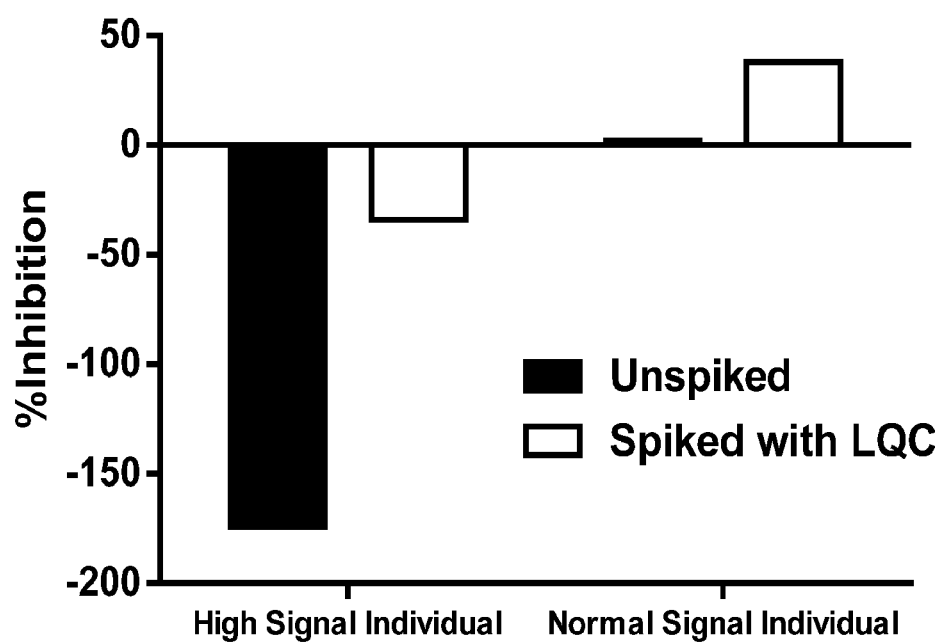

FIGS. 9 and 10 show the results in the drug capture format of studies of mitigation of high signal response human samples which interfere in the detection of NAb. FIG. 9 shows the results in high signal response in selected rheumatoid factor positive (RF+) individuals; FIG. 10 shows the results in NAb recovery in high signal RF+ individuals.

Figure 11:
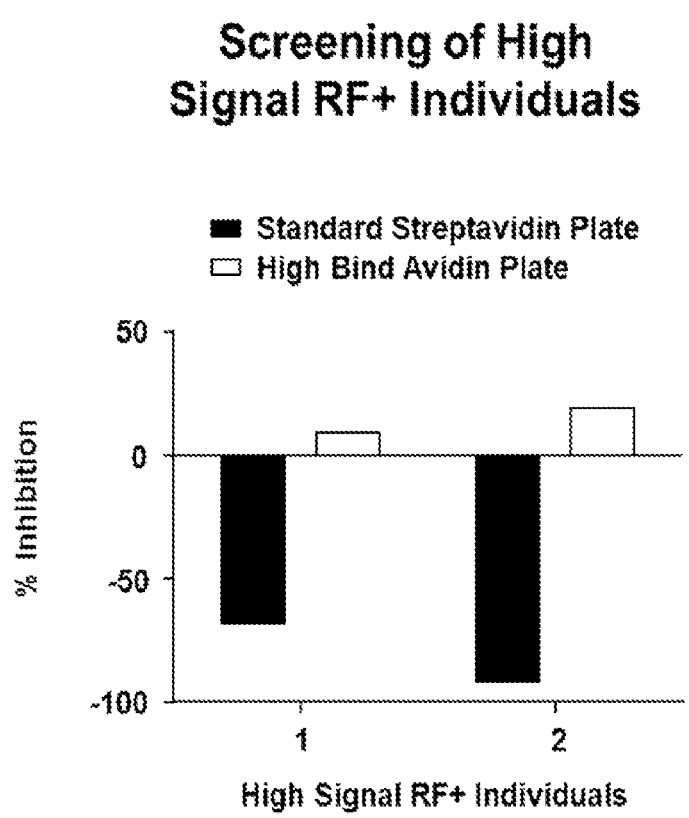

FIG. 11 is a bar graph of results obtained from screening high signal RF+ individuals in standard streptavidin (solid bar) or high bind avidin (open bar) plates.

Figure 12:
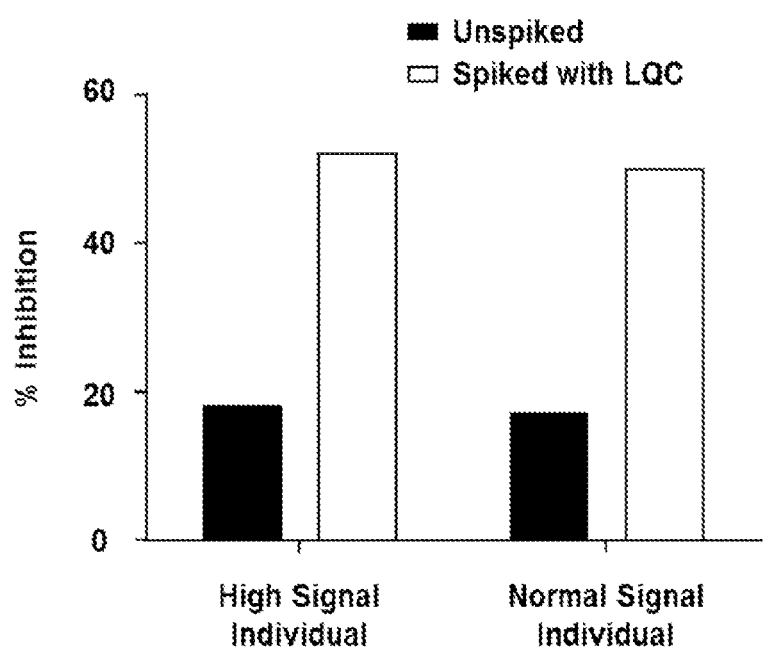

FIG. 12 is a bar graph showing results obtained in selected high signal RF+ individuals or normal signal RF+ individual; solid bar=unspiked sample; open bar=sample spiked with LQC.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety. Other embodiments will become apparent from a review of the ensuing detailed description.

In order that the invention herein described may be fully understood, the following detailed description is set forth.

Figure 1:
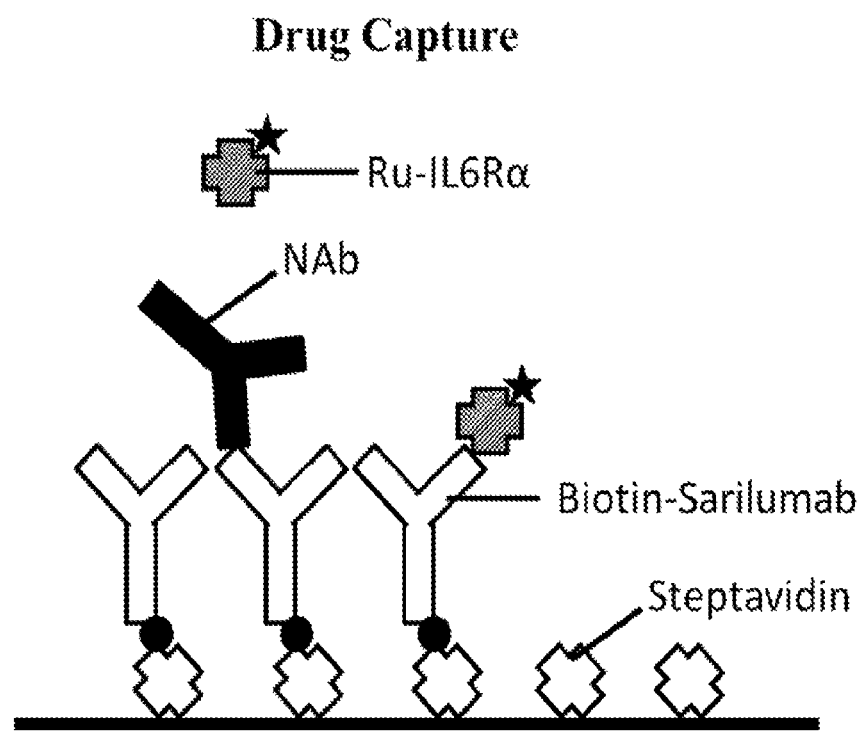
FIGS. 1 and 2 illustrate and compare drug capture (FIG. 1) and target capture (FIG. 2) assay formats. In both assay formats, a signal is generated in the absence of NAbs and an inhibition of signal occurs in the presence of NAbs. % Inhibition=% reduction of the background (NQC) signal caused by the presence of NAb.
Figure 2:
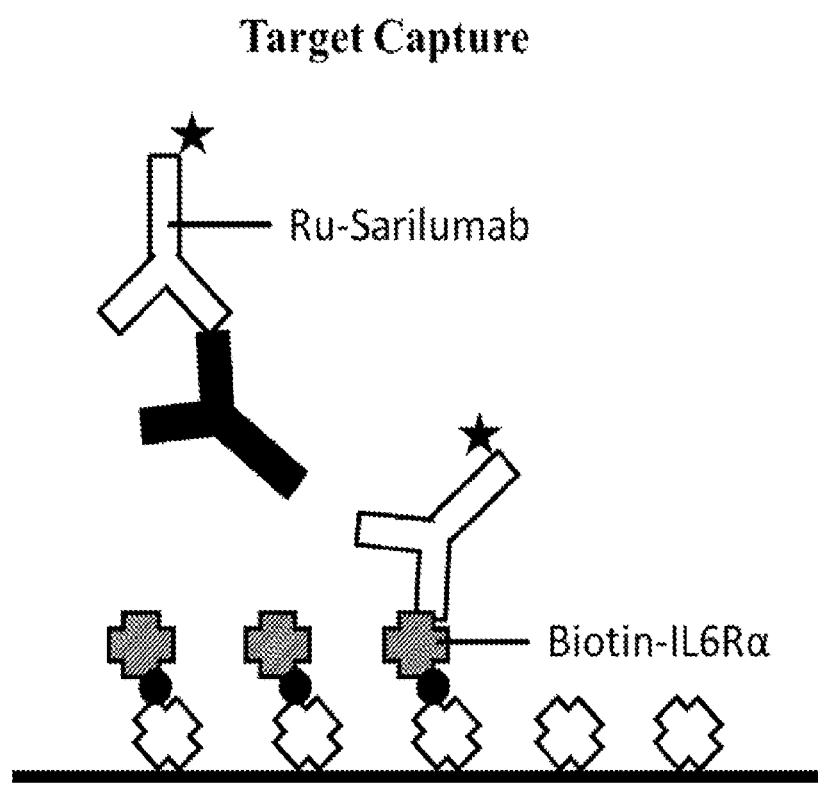

The CLB assay developed here was based on the Meso Scale Discovery (MSD) platform. FIGS. 1 and 2 illustrate the two assay formats investigated. FIG. 1 illustrates the drug capture format in which NAbs in human serum sample were incubated with biotinylated-sarilumab and subsequently captured on a streptavidin- or avidin coated microplate. Addition of ruthenylated-IL6Rα then resulted in signal in the absence of NAbs and an inhibition of the signal in the presence of NAbs. The principle remains the same in the target capture format, except ruthenylated-sarilumab is now captured by biotinylated-IL6Rα target on the plate. Development of a sensitive and reliable assay included optimization of drug, target, label, pH and incubation times. The two assay formats were compared and the superior format was then optimized and validated.

Initial characterization suggested that the target capture was more susceptible to drug interference, while the drug capture format resulted in higher non-specific signals. Several optimization strategies were examined followed by a comparative evaluation to select the best assay for this program. The high background signal leading to false negative results from RF+ serum was effectively eliminated by switching to a different solid substrate of avidin-coated microplates. Low pH treatment improved drug tolerance, while target interference was mitigated with an anti-target antibody that specifically blocks the interaction between the target and the drug. Results showed that the drug capture format provided a sensitive and robust assay with minimal interference from either target or drug. The validated assay demonstrated precision ranging from 1-8% with the following characteristics: Sensitivity=~150 ng/mL, Drug Tolerance=~500 ng/mL, Target interference=~1 µg/mL.

Although target capture and drug capture formats can both be used successfully to establish CLB NAb assays, it is important to study the specific binding characteristics of the drug and target pair to devise successful strategies for sensitivity, drug tolerance, and mitigating target interference. Based on the results obtained, the drug capture format was superior and thus validated and utilized for clinical sample bioanalysis.

The invention features an immunogenicity assay for the detection of neutralizing antibodies to a protein biotherapeutic. In one embodiment, the protein biotherapeutic is a monoclonal antibody (mAb); more specifically, the protein biotherapeutic is a mAb that specifically binds interleukin-6 receptor alpha (IL-6Rα); more specifically the biotherapeutic is sarilumab. Sarilumab (also called REGN88) has been developed for the treatment of rheumatoid arthritis. Accordingly, in a specific embodiment the invention presents an immunogenicity assay for the detection of neutralizing antibodies in a patient treated for rheumatoid arthritis with sarilumab. It is envisioned that other anti-IL-6Rα monoclonal antibodies can be used in the method of the invention, for example, the humanized anti-IL-6Rα tocelizumab.

Definitions

"Neutralizing antibody (NAb)" is an anti-drug antibody having the ability to neutralize the biotherapeutic molecule. In one embodiment, the biotherapeutic molecule is the anti-IL6Rα antibody sarilumab, and the NAb binds the IL6Rα antibody and prevents it from binding IL6Rα.

The term "analyte" is used to refer to the substance being analyzed, i.e., mouse anti-REGN88 monoclonal antibody (REGN575) present in quality controls or human anti-REGN88 NAbs in human serum samples.

"Cut point" is a term referring to a threshold value (i.e., % inhibition) used to distinguish between a NAb negative and a NAb positive response in the assay. It is a constant value, determined statistically by analyzing assay responses of a set of drug-naïve diseased human samples.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Competitive Ligand Binding Assay for Detecting NAbs to REGN88 (Sarilumab)

REGN88 is a human monoclonal antibody (IgG1 subclass) specific for human Interleukin-6 receptor α (IL-6Rα). A method to detect anti-REGN88 neutralizing antibodies (NAb) using a competitive ligand binding assay format was developed as described below.

The assay procedure employs a mouse anti-REGN88 monoclonal antibody (REGN575) as the positive control, biotinylated REGN88 (Biotinylated-REGN88) as the capture reagent, ruthenium-labeled soluble hIL-6Rα (ruthenium-REGN78) as the detection reagent, and REGN17 (an anti-human IL-6Rα monoclonal antibody) to mitigate ligand interference.

Briefly, samples and controls are diluted in low pH conditions (with acetic acid) and then neutralized using a Tris-base solution containing Biotinylated-REGN88 and REGN17. The low pH treatment results in the dissociation of NAb:drug and drug:target complexes present in serum samples, allowing for improved detection of NAb in the presence of excess drug in the serum. In order to mitigate target interference, REGN17 is used to bind free target released by the low pH treatment. During the incubation, the positive control (REGN575) or any NAb present in the sample binds to the biotinylated-REGN88. The low pH treated samples were then added to the avidin precoated microplate, where the avidin captured the biotinylated-REGN88 along with any NAb that was bound to it.

After incubation and washing, ruthenium-REGN78 was added to the microplate. In the absence of NAb in the sample, the avidin captured biotinylated-REGN88 binds to the ruthenium-REGN78 forming a biotinylated-REGN88:ruthenium-REGN78 complex on the surface of the microplate. A tripropylamine (TPA) based read buffer was added to the microplate which was read by a Meso Scale Discovery (MSD) electrochemiluminescence reader. In the presence of NAb, the NAb will bind the biotinylated-REGN88 preventing the formation of the biotinylated-REGN88:ruthenium-REGN78 complex which in turn reduces the electrochemiluminescent signal. Hence, the measured electrochemiluminescence (i.e., counts) is inversely proportional to the amount of NAb in the sample.

Eighty drug-naïve patient samples were analyzed to determine the cut point. The selected % inhibition cut point was 40, calculated using a parametric method based on a 0.1% false positive rate. Percent Inhibition (% Inhibition) was calculated as the decrease in signal resulting from the presence of NAb. Positive Quality Control (PQC) were control samples with a known amount of REGN575, prepared in NQC, used to verify the assay's performance: HQC=High Quality Control; 20×HQC: 4 µg/mL; MQC=Mid Quality Control; 20 MQC: 0.4 µg/mL; LQC=Low Quality Control; 20×LQC: 0.2 µg/mL. Negative Quality Control (NQC) were control samples without analyte (neat human serum), used to calculate % Inhibition. Spiked Negative Quality Control (SNQC) were control samples with a known amount of REGN78, prepared in NQC, used to verify REGN17's performance CV %—Coefficient of variation expressed as a percentage. Limit of Detection (LOD) was the lowest concentration of the positive control (REGN575) with a % Inhibition that is greater than the cut point. The LOD of the assay in neat serum was approximately 150 ng/mL of mouse anti-REGN88 monoclonal antibody (REGN575). Counts=unit of electrochemiluminescence signal.

Materials and Equipment.

Reagents: Mouse anti-REGN88 monoclonal antibody (Regeneron, REGN575) also referred to as anti-REGN88 mAb; biotinylated REGN88 (biotin-REGN88 or biotinylated-REGN88); ruthenium-labeled hIL-6Rα (Ru(bpy)3 REGN78 or ruthenium-REGN78); mouse anti-human IL-6Rα monoclonal antibody (also referred to as anti-hIL-6Rα mAb); hIL-6Rα (REGN78); 5% BSA blocking buffer; phosphate buffered aaline, pH 7.2 (1×PBS); avidin-coated microplate—MULTI-ARRAY® 96-well Avidin Gold Plate; 300 mM acetic acid; 1.5 M Trizma-base solution (Tris or Tris-base); read buffer—MSD Read Buffer T (4×), with surfactant (4× Read Buffer); 1× wash buffer; purified water; pooled human serum.

Instruments and Labware.

96-well polypropylene plate (deep well plate or block); Sector Imager 2400 (Meso Scale Discovery, Model 1250) with accompanying MSD Discovery Workbench application; Microsoft Excel; SoftMax® Pro application, version 5.2 or higher (Molecular Devices).

Procedure.

Plate shaking was performed during the incubation steps. A minimum of 10 µL was used for all volume transfers. Biosafety Level 2 precautions were adhered to when handling human serum. Quality Controls (QCs): QCs were shown to be stable for up to 10 freeze-thaw cycles, storage at room temperature for at least 4 hours (4 hours and 32 minutes), or storage in a 4° C. refrigerator up to 23 hours (23 hours and 20 minutes). QC stability was used as a surrogate for study sample stability. Negative Quality Control (NQC): A commercial normal human serum pool was qualified for use as the NQC. Aliquots the human serum pool (NQC) and store in a −80° C. freezer.

Preparation of PQCs—(HQC, MQC, LQC).

PQCs were qualified if they are intended for use in sample analysis after the day of preparation. 20×PQCs were prepared at the concentrations listed in the table below, by spiking mouse anti-REGN88 monoclonal antibody (REGN575) into NQC. The following may be used as an example for the preparation of each PQC: Example: 10 µL of REGN575 (0.88 mg/mL) was added to 166 µL of NQC and mixed to yield a 50 µg/mL REGN575 solution (QC Precursor A). 10 µL of the 50 µg/mL REGN575 solution was added to 490 µL of NQC and mix to yield a 1 µg/mL REGN575 solution (QC Precursor B). PQCs may be used on the same day or may be aliquoted and stored in a −80° C. freezer.

| Quality Controls | 20X QC Concentration | 1X Assay Concentration | Volume of QC Precursor (μL) | Volume of NQC (μL) |
|---|---|---|---|---|
| HQC | 4 μg/mL | 200 ng/mL | 40 (Precursor A) | 460 |
| MQC | 0.4 μg/mL | 20 ng/mL | 200 (Precursor B) | 300 |
| LQC | 0.2 μg/mL | 10 ng/mL | 100 (Precursor B) | 400 |

Spiked Negative Quality Control (SNQC).

SNQC were qualified for use in sample analysis after the day of preparation. A solution of 0.6 μg/mL hIL-6Rα (REGN78) was prepared in NQC. The following may be used as an example for the preparation of the SNQC: Example: 10 μL of REGN78 (2.3 mg/mL) was added to 220 μL of NQC and mixed to yield a 100 μg/mL REGN78 solution. 10 μL of the 100 μg/mL REGN78 solution was added to 90 μL of NQC and mixed to yield a 10 μg/mL REGN78 solution. 30 μL of the 10 μg/mL REGN78 solution was added to 470 μL of NQC and mixed to yield a 0.6 μg/mL REGN78 solution (SNQC). The SNQC was used on the same day or aliquoted and stored in a −80° C. freezer.

Assay Procedure.

QCs were retrieved and thawed, and study samples kept on ice or in a 4° C. refrigerator. In a deep well polypropylene plate (Sample Plate), a 1:10 dilution of each QC and study sample was prepared in 300 mM acetic acid and mixed. Example: 10 μL of each QC/sample was added to 90 μL of 300 mM acetic acid and mixed. The Sample Plate was covered and incubate for 45±15 minutes at room temperature. A 1% BSA solution in 1×PBS was prepared and mixed. Example: 8 mL of 5% BSA Blocking Buffer was added to 32 mL of 1×PBS and mixed. A solution containing 10 ng/mL of biotinylated-REGN88, 50 μg/mL of REGN17, and 0.2 M Tris in 1% BSA was prepared and mixed. Example: 10 μL of biotinylated-REGN88 (3.8 mg/mL) was added to 370 μL of 1% BSA and mixed to yield a 100 μg/mL biotinylated-REGN88 solution. 10 μL of the 100 μg/mL biotinylated-REGN88 was added to 190 μL of 1% BSA and mixed to yield a 5 μg/mL biotinylated-REGN88 solution. 15 μL of the 5 μg/mL biotinylated-REGN88, 19.3 μL of the 19.5 mg/mL REGN17, and 1 mL of 1.5 M Trizma Base was added to 6.5 mL of 1% BSA and mixed to yield a 10 ng/mL biotinylated-REGN88, 50 μg/mL REGN17, and 0.2 M Tris in 1% BSA solution. In a deep well polypropylene plate (Sample Plate) a final 1:2 dilution (1:20 total dilution) of the QCs and study samples were prepared in the 10 ng/mL biotinylated-REGN88, 50 μg/mL REGN17, and 0.2 M Tris in 1% BSA solution and mixed. Example: 100 μL of 10 ng/mL Biotinylated-REGN88, 50 μg/mL REGN17, and 0.2 M Tris in 1% BSA solution were added to 100 μL of acidified QCs/samples and mix. The sample plate was covered and incubated for 60±15 minutes at room temperature, shaking at 400 rpm during the incubation. The assay plate 3× was washed with 300 μL/well of 1× Wash Buffer using the MSD PLATE 3× wash program. 50 μL of each QC and study sample were added from the Sample Plate to the Assay Plate in duplicate. The Assay Plate was covered and incubated for 60±15 minutes at room temperature, shaking at 400 rpm during the incubation. A solution containing 2 μg/mL of ruthenium-REGN78 in 1% BSA was prepared and mixed. Example: Add 10 μL of ruthenium-REGN78 (2.9 mg/mL) to 280 μL of 1% BSA and mix to yield a 100 μg/mL ruthenium-REGN78 solution. 140 μL of the 100 μg/mL ruthenium-REGN78 was displaced into 7 mL of 1% BSA and mixed to yield a 2 μg/mL ruthenium-REGN78 in 1% BSA solution. The Assay Plate 3× was washed with 300 μL/well of 1× Wash Buffer using the MSD_PLATE_3× wash program. 50 μL/well of the 2 μg/mL ruthenium-REGN78 in 1% BSA solution was added to the Assay Plate. The Assay Plate was covered and incubated for 60±15 minutes at room temperature, shaking at 400 rpm during the incubation. Microplate Preparation. 300 μL/well of 5% BSA Blocking Buffer was added to the avidin-coated microplate (Assay Plate). The microplate was sealed and incubated for 1 to 4 hours at room temperature. A 2× Read Buffer solution was prepared and mixed. Example: 10 mL of 4× Read Buffer was added to 10 mL of purified water and mixed. The Assay Plate 3× was washed with 300 μL/well of 1× Wash Buffer using the MSD_PLATE_3× wash program. 150 μL/well of the 2× Read Buffer solution was added to the Assay Plate. The Assay Plate was read on a Sector Imager 2400 within 10 minutes after addition of 2× Read Buffer.

Data Analysis.

The plate reading data was transferred it to a SoftMax Pro file format. Once in the SoftMax file, if mask wells were needed, wells were masked in the Transformed Data section. This allowed the masked value to be viewed, but not used in the calculations. The mean counts, % Inhibition, and CV % Counts were then calculated for each QC and study sample.

% Inhibition=100×[(Mean Counts of NQC−Mean Counts of PQC or sample)/Mean Counts of NQC].

Assay Performance Specifications:

LQC % Inhibition must be >Cut point; SNQC % Inhibition must be <Cut point; HQC % Inhibition must be >MQC % Inhibition; MQC % Inhibition must be >LQC % Inhibition; The CV % Counts of each PQC and the SNQC must be ≤20%; The CV % Counts of the NQC must be ≤15%.

Study Sample Acceptance Criteria. Assay Performance—All assay performance specifications were met, otherwise the study samples were re-documented and re-analyzed. Precision—The CV % Counts had to be ≤20%, otherwise the study samples were re-documented and re-analyzed. Any study sample with a % Inhibition greater than the cut point was reported as Positive. Any study sample with a % Inhibition less than or equal to the cut point was reported as Negative.

Example 2. Influence of Low pH Treatment on Drug Tolerance

Figure 3:
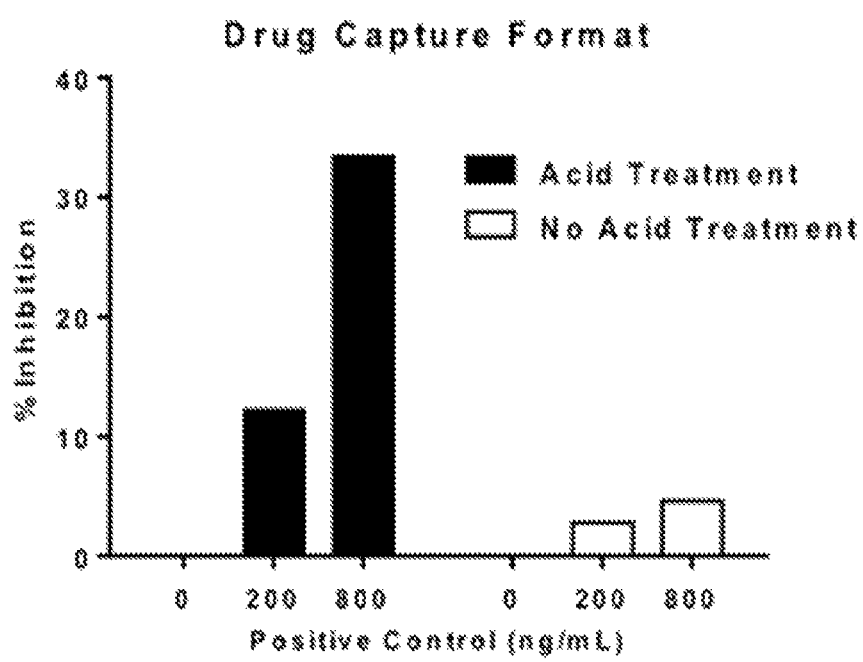
FIGS. 3 and 4 are bar graphs showing the effect of low pH treatment on drug tolerance for the drug capture (FIG. 3) and target capture (FIG. 4) assay formats. solid=low pH treatment; empty=no low pH treatment.
Figure 4:
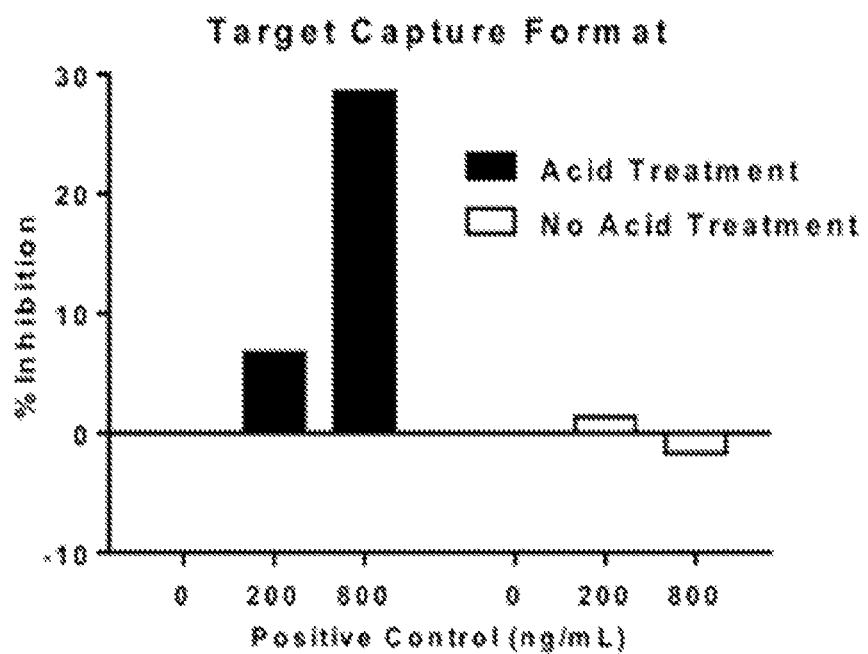

An experiment was conducted to test the effect of low pH treatment on drug tolerance in both the drug capture and target capture formats. Human serum was spiked with 1 μg/mL of sarilumab at the indicated concentrations of positive control. These samples were tested with or without low pH treatment in both assay formats. QCs and samples were diluted in an acetic acid working stock concentration and incubated. These were then diluted in a Tris neutralization buffer containing the appropriate ruthenylated-detection reagent. The results are shown in FIGS. 3 and 4.

Results:

Low pH treatment effectively mitigates the interference from excess drug, improving the detection of NAb in both assay formats.

Example 3. Drug Interference

The ability of the drug to generate a false positive response in the absence of NAb is defined as drug interference. A study was conducted to compare the interference of drug in the absence of NAb in both assay formats.

Method:

Normal human serum was spiked with the indicated concentrations of sarilumab. All samples were treated in low pH and tested in both the drug capture format and the target capture format.

Results.

Figure 5:
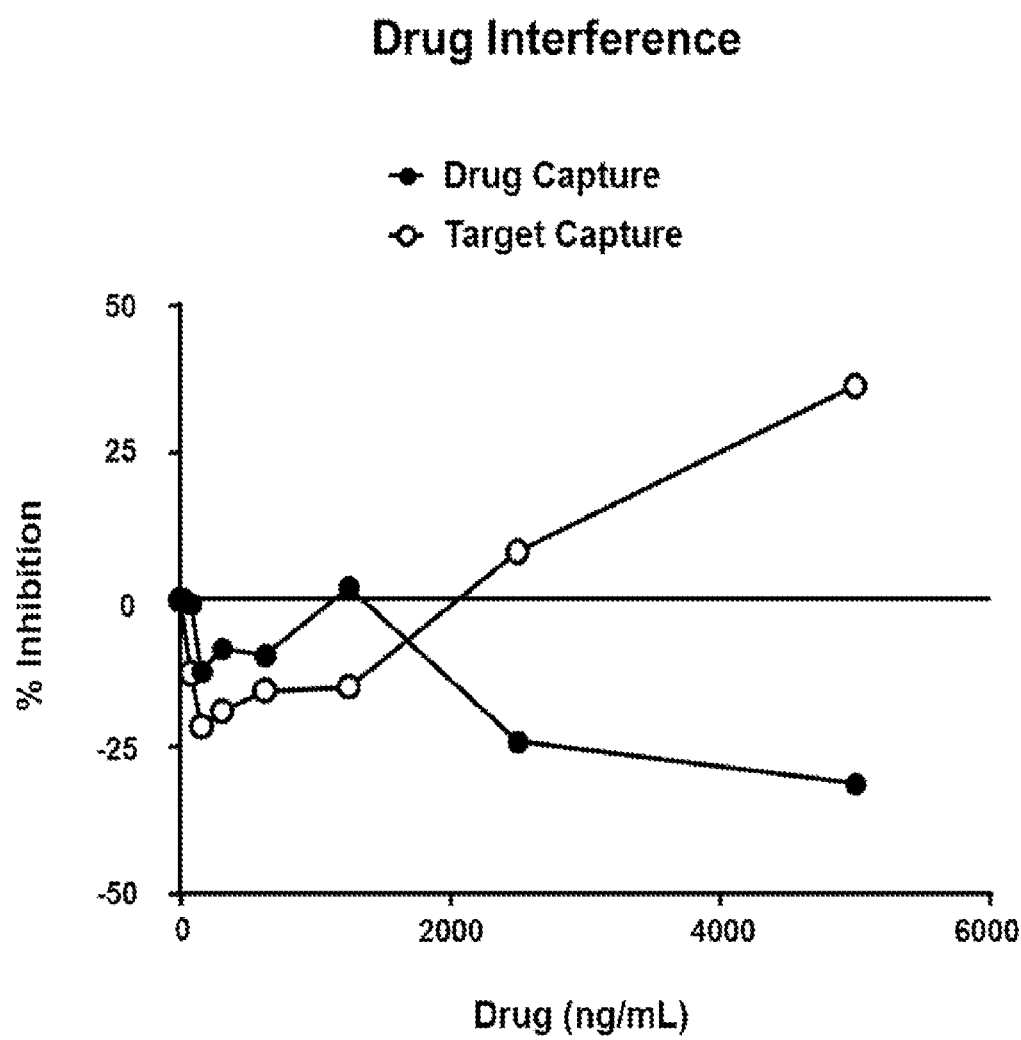
FIGS. 5 and 6 show the effects of drug interference in drug capture (FIG. 5) and target capture (FIG. 6) assay formats.
Figure 6:
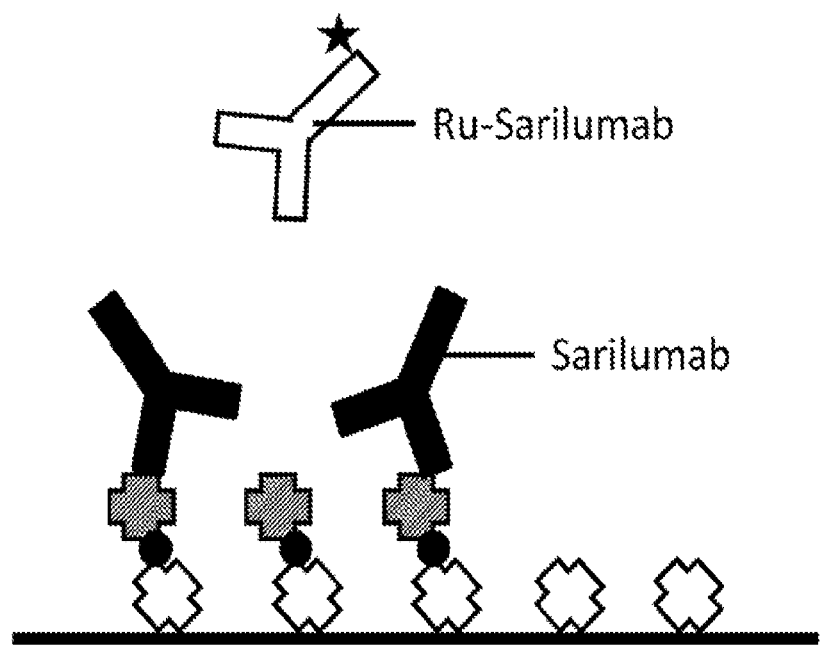

Target capture format: Higher concentrations of free sarilumab outcompete the ruthenylated-sarilumab for binding with the biotinylated-IL6Rα, resulting in a false positive response (FIG. 5). Drug capture format: Sarilumab in the absence of NAb cannot bind to the capturing sarilumab on the plate and is therefore unable to interfere in the assay (FIG. 6).

The effect of specific target IL6Rα on the mitigation of false positive results was studied as described above. Normal human serum was spiked with the indicated concentrations of IL6Rα and tested with low pH treatment in both assay formats (FIG. 7). Similar samples were tested with or without the addition of an anti-target (IL6Rα) antibody (FIG. 8). False positive responses from target interference were observed in both assay formats. Similar results were observed when IL6Rα:sarilumab complexes were tested. Addition of an anti-target antibody mitigated the interference in the drug capture format. However, the anti-target antibody cannot be added to the target capture format since it would block capture. The drug capture format was selected and used from this point on.

A study was conducted to mitigate false positive results caused by target (IL6Rα). Normal human serum was spiked with the indicated concentrations of IL6Rα and tested with low pH treatment in both assay formats. Similar samples were tested with or without the addition of an anti-target (IL6Rα) antibody.

False positive responses from target interference were observed in both assay formats (FIG. 7). Similar results were observed when IL6Rα:sarilumab complexes were tested (FIG. 8). Addition of an anti-target antibody mitigated the interference in the drug capture format. However, the anti-target antibody cannot be added to the target capture format since it would block capture. The drug capture format was selected and used from this point on.

Example 4. Mitigation of Human Serum Matrix Interference

Next, RF+ serums were treated in low pH and screened in the drug capture format. Comparison between a selected high signal RF+ individual versus a normal signal RF+ individual. Positive control at LQC level was spiked in these drug naïve serums before low pH treatment and then run in the assay.

Results:

The signal generated by certain RF+ individuals was greater than the signal of the NQC and resulted in highly negative % Inhibitions. In these individuals, spiking with positive control still resulted in false negative results (FIGS. 9 and 10).

A study was conducted comparing between standard streptavidin-coated plates versus high bind avidin-coated plates. Two high signal RF+ individuals were treated in low pH and tested in the assay. Then, a comparison between a selected high signal RF+ individual versus a normal signal RF+ individual was conducted. Positive control at the LQC level was spiked in these drug naïve sera before low pH treatment and then run on a high bind avidin-coated plate.

Results:

High signal RF+ individuals could be normalized by changing to high bind avidin-coated plates (FIG. 11). By normalizing the signals, these plates allowed the detection of NAb in these "high signal" RF+ individuals (FIG. 12).

What is claimed is:

1. A method for detecting the presence of neutralizing antibodies to a biotherapeutic protein, wherein the biotherapeutic protein has been administered to a patient in need, comprising the steps of (a) decreasing the pH of the patient sample to an acidic pH, (b) combining the patient sample with an antibody that binds to a target of the biotherapeutic protein and a capture reagent comprising a labeled biotherapeutic protein, wherein the label on the biotherapeutic protein facilitating binding of the biotherapeutic protein to a surface, and (c) adding a detecting reagent comprising a labeled target of the biotherapeutic protein, wherein a decreased signal relative to a control sample indicates the presence of a neutralizing antibody to the biotherapeutic protein.

2. The method of claim 1, wherein the protein biotherapeutic is a monoclonal antibody.

3. The method of claim 2, wherein the protein biotherapeutic is an anti-interleukin-6 receptor α (IL-6Rα) monoclonal antibody.

4. The method of claim 3, wherein the protein biotherapeutic is sarilumab or tocilizumab.

5. The method of claim 4, wherein the protein biotherapeutic is sarilumab.

6. The method of claim 1, wherein the patient is treated for an IL-6-dependent disease.

7. The method of claim 6, wherein the IL-6-dependent disease is one of rheumatoid arthritis, diabetes, atherosclerosis, Alzheimer's disease, systemic lupus erythematosus, multiple myeloma, connective tissue disorders, Castleman's disease and prostate cancer.

8. The method of claim 7, wherein the IL-6-dependent disease is rheumatoid arthritis.

9. The method of claim 1, wherein the capture reagent is labeled sarilumab.

10. The method of claim 9, wherein the labeled sarilumab is biotinylated sarilumab.

11. The method of claim 10, wherein the biotinylated sarilumab is bound to an avidin-coated plate.

12. The method of claim 1, wherein the target is soluble IL-6 receptor α.

13. The method of claim 1, wherein the labeled target is ruthenium labeled soluble IL-6 receptor α.

14. The method of claim 1, wherein the pH of the patient sample is decreased to an acidic pH by treatment with an acidic solution.

15. The method of claim 1, further comprising increasing the pH of the patient sample to a neutral pH following the decrease of the patient sample to an acidic pH.

16. The method of claim 1, wherein the method exhibits a sensitivity tolerance of about 150 ng/mL, a drug tolerance of about 500 ng/mL, and a target interference tolerance of about 1 μg/mL.

17. A method for detecting the presence of neutralizing antibodies to sarilumab, wherein sarilumab has been administered to a patient in need, comprising the steps of (a) decreasing the pH of a serum sample to an acidic pH; (b) combining a patient serum sample with a capture reagent comprising biotinylated sarilumab; (c) increasing the pH of the combined serum sample and capture reagent to a neutral pH; and (d) adding a detecting reagent, wherein the detecting reagent comprises labeled soluble IL-6 receptor α, wherein a decreased signal relative to a control sample indicates the presence of a neutralizing antibody to sarilumab.

18. The method of claim 17, wherein the detecting reagent is ruthenium labeled soluble IL-6 receptor α.

19. The method of claim 17, wherein the patient is suffering from rheumatoid arthritis.

20. The method of claim 17, wherein the method exhibits a sensitivity tolerance of about 150 ng/mL, a drug tolerance of about 500 ng/mL, and a target interference tolerance of about 1 μg/mL.

21. The method of claim 14, wherein the acidic solution is acetic acid.

22. The method of claim 15, wherein the pH is increased to a neutral pH by treatment with a basic solution.

23. The method of claim 22, wherein the basic solution is a Tris base.

24. The method of claim 17, wherein the pH is decreased to an acidic pH by treatment with an acid solution.

25. The method of claim 24, wherein the acidic solution is acetic acid.

26. The method of claim 17, wherein the pH is increased to a neutral pH by treatment with a basic solution.

27. The method of claim 26, wherein the basic solution is a Tris base.

28. The method of claim 1, wherein the label of the labeled biotherapeutic-protein is biotin.

29. The method of claim 1, wherein the antibody binds free target of the biotherapeutic protein released by the low pH treatment and mitigates target interference.

* * * * *